United States Patent [19]

Ramakrishnan

[11] Patent Number: 5,395,938
[45] Date of Patent: Mar. 7, 1995

[54] BIOTINYLATED CHEMILUMINESCENT LABELS AND THEIR CONJUGATES, ASSAYS AND ASSAY KITS

[75] Inventor: Kastooriranganathan Ramakrishnan, Eden Prairie, Minn.

[73] Assignee: Nichols Institute Diagnostics, San Juan Capistrano, Calif.

[21] Appl. No.: 933,478

[22] Filed: Aug. 21, 1992

[51] Int. Cl.$^6$ ............................................. C07D 495/04
[52] U.S. Cl. .................................. 546/104; 548/303.7; 548/304.1; 530/408; 530/409; 436/501; 435/7.5
[58] Field of Search ..................... 546/104; 548/303.7, 548/304.1; 435/7.5; 436/501; 530/408, 409

[56] References Cited

U.S. PATENT DOCUMENTS 5,162,352 11/1992 Hall et al. ............................ 514/374
5,180,828 1/1993 Ghazarossian et al. .............. 546/37

*Primary Examiner*—Richard L. Raymond
*Attorney, Agent, or Firm*—Dorsey & Whitney

[57] ABSTRACT

A unique class of chemiluminescent labels containing biotin substitution that are suitable for chemiluminescent assays using inter alia a streptavidin and/or avidin conjugate. The chemiluminescent labels of the invention have the ability to bind to streptavidin and/or avidin per se or to streptavidin and/or avidin conjugated with an analyte. Label structures are disclosed that have hydrolytic stability to meet the most demanding commercial assay conditions. The invention encompasses conjugates containing associated versions of the labeling compounds, assays and kits for performing such assay utilizing the conjugates.

29 Claims, No Drawings

BIOTINYLATED CHEMILUMINESCENT LABELS AND THEIR CONJUGATES, ASSAYS AND ASSAY KITS

BRIEF DESCRIPTION OF THE INVENTION

This invention relates to a unique class of chemiluminescent labels containing biotin substitution that are suitable for chemiluminescent assays using inter alia a streptavidin and/or avidin conjugate. The chemiluminescent labels of the invention have the ability to bind to streptavidin and/or avidin per se or to streptavidin and/or avidin conjugated with an analyte. Label structures are disclosed that have hydrolyric stability to meet the most demanding commercial assay conditions. The invention encompasses conjugates containing associated versions of the labeling compounds, assays and kits for performing such assay utilizing the conjugates.

BACKGROUND OF THE INVENTION

The literature describes classes of compounds that give off light or "luminesce" by reaction through chemical treatment, e.g., with peroxide or molecular oxygen at high pH. The compounds that have this capability are termed chemiluminescent materials. Light is produced by the decay of the transient ("intermediate") structure formed by peroxide or molecular oxygen induced reaction at an $sp^2$ or $sp^3$ hybridized carbon in the compound that is part of a chain or a ring or ring system.

As the literature indicates, any series of reactions which produce the intermediate:

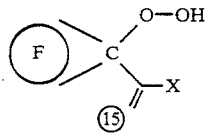

will lead to moderate to strong chemiluminescence. is a structure such that the product carbonyl derivative

is fluorescent and X is a good leaving group, usually with XH, for efficient chemiluminescence, having a $pK_a$ of about $\leq 11$, preferably $<11$, and most preferably, from about 5 to about 8. The reaction may require base catalysis. The intermediate can be prepared (in isolable or transient form, depending on ⑤) from species such as:

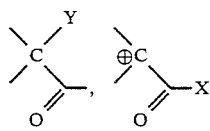

and $H_2O_2$ (Y is halogen, $-SO_2R$, and the like) or

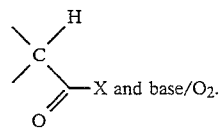

X and base/$O_2$.

and base/$O_2$.

See *Endeavour*, 23, No. 117 (1973) p. 140, *The Chemistry of Bioluminescence* in "*Bioluminescence in Action*" (P. J. Herring, ed.), Academic Press, London, 1978 (pp. 64–5), *Proc. R. Soc. Lond.*, B 215, p. 256 (1982), *Progress in Organic Chemistry*, (W. Carruthers and J. K. Sutherland, eds.), Butterworth, London (1973), p. 261, all authored by F. McCapra.

For example, chemiluminescent aryl esters that contain such hybridized carbon, termed a labeling compound, react according to the following general reaction:

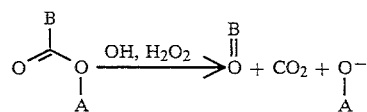

where A is an aryl ring or ring system and B is a heterocyclic ring or ring system. In this reaction, —O—A, the leaving group, is cleaved by perhydrolysis resulting in steps leading to the transient intermediate, B=O, that proceeds to decay generating luminescence.

The characteristics of some of these chemiluminescent compounds, their chemistry of manufacture, and other factors relating to them, are more fully described by McCapra, "Chemiluminescence of Organic Compounds," in Progress in Organic Chemistry, vol. 8, Carruthers and Sutherland ed., Wiley & Sons (1973); Kohen, Bayer, Wilechek, Barnard, Kim, Colleins, Beheshti, Richardson and McCapra, "Development Of Luminescence-Based Immunoassays For Haptens And For Peptide Hormones," pp. 149-158, in *Analytical Applications Of Bioluminescence and Chemiluminescence*, Academic Press, Inc. (1984); Richardson, Kirn, Barnard, Collins and McCapra, *Clinical Chemistry*, vol. 31, no. 10, pp. 1664-1668 (1985); McCapra, "The Application of Chemiluminescence in Diagnostics," 40th Conference of the American Association of Clinical Chemists, New Orleans, La., Jul. 28, 1988; McCapra, "The Chemiluminescence Of Organic Compounds," Quarterly Reviews, vol. 20, pp. 485-510 (1966); McCapra, "The Chemiluminescence Of Organic Compounds," *Pure and Applied Chemistry*, vol. 24, pp. 611-629 (1970); McCapra, "The chemistry of bioluminescence," *Proceedings Of Royal Society*, vol. B215, pp. 247-278 (1982); McCapra and Beheshti, "Selected Chemical Reactions That Produce Light," *Bioluminescence and Chemiluminescence: Instruments and Applications*, CRC Press, vol. 1, Chapter 2, pp. 9-37 (1985); McCapra, "Chemiluminescent Reactions of Acridines," Chapt. IX, *Acridines*, R. M. Acheson, Ed., pp. 615-630, John Wiley & Sons, Inc. (1973); McCapra, "Chemical Mechanisms in Bioluminescence," *Accounts Of Chemical Research*, vol. 9, no. 6, pp. 201-208 (June 1976); and in many other publications and presentations on the subject.

As noted in the above literature, chemiluminescent compounds of a variety of structures have been projected as labels for a variety of assays including immunoassays (in this respect, see U.S. Pat. Nos. 4,383,031, 4,380,580 and 4,226,993). The esters, thiolesters and amides, alone or conjugated (i.e., chemically coupled to another material), are especially desirable forms of chemiluminescent labels. However, they lose their luminescence capability over time in an aqueous system because they hydrolyze to products that are not available to the assay. Until recently, these compounds have not been used in commercial assays. Until this invention, the ester, thiolester and amide forms of this class of materials lacked sufficient hydrolytic stability to be stored in the most convenient form over an extended period of time, which is as a component of an aqueous system.

It is well understood in chemistry that carboxylic acid esters, thiolesters and amides are susceptible to hydrolytic attack resulting in the formation of the carboxylic acid and the hydroxy, mercapto or amino component that is the theoretical or actual precursor to the ester, thiolester or amide. Hydrolysis is more pronounced under acid or basic conditions. It is also recognized in chemistry that certain levels of hydrolysis can be inhibited by the inclusion of properly positioned bulky groups that chemically sterically hinder those linkages, see Nishioka et al., *J. Org. Chem.*, vol. 40, no. 17, pp. 2520–2525 (1975), Fujita et al, "The Analysis of the Ortho Effect," *Progress in Physical Organic Chemistry*, 8, pp. 49–89 (1976), Morrison and Boyd, *Organic Chemistry*, 5$^{th}$ Ed., pp. 842–843 (1987) and March, *Advanced Organic Chemistry*, 3rd Ed., Publ. by John Wiley & Sons, New York, N.Y. (1985) page 240. According to March:

"Another example of steric hindrance is found in 2,6-disubstituted benzoic acids, which are difficult to esterfly no matter what the resonance or field effects of the groups in the 2 or the 6 position. Similarly, once the 2,6-disubstituted benzoic acids are esterified, the esters are difficult to hydrolyze."

(Emphasis in the original)

The difficulty in esterification is not the same in making esters from 2,6-substituted phenols, but the general principles described by March are applicable to enhancing the hydrolytic stability of the resultant ester so long as the ortho substitutions are electron donating. As this invention demonstrates, effective levels of hydrolytic stability require the presence of a select level of electron withdrawing chemical effect in conjunction with (and in addition to) traditional chemical steric hindrance factors.

The functional electron withdrawing or electron donating characteristics of a group in an organic compound is conventionally measured relative to hydrogen. This relative ranking accepts that all groups on a molecule will provide some slectron withdrawing effect, and distinquishes them by the nature of impact the group has on the molecule's performance. An electron withdrawing functional group, characterized by a positive number, will draw electrons to itself more than hydrogen would if it occupied the same position in the molecule. The opposite occurs with an "electron donating group," a lesser electron withdrawing group which chemical convention characterizes by a negative number. Sigma para values ($\sigma_p$) are the relative measurement of electron withdrawing or electron donating qualities of a functional group in the para position on benzoic acid. See March, supra, at pp. 242–250 and 617–8. Tables of $\sigma_p$ values for various groups can be found in Hansch et al., *J. Med. Chem.*, 16(11):1209–1213 (1977) and Hansch and Leo, "Substituent Constants for Correlation Analysis in Chemistry and Biology," Ch. 6, pp. 49–52 (John Wiley & Sons, New York 1979). The $\sigma_p$ values reported in the Hansch articles are relied on herein in characterizing relative values for groups both in the meta and para position.

Biotin, a water-soluble factor of the vitamin B complex and a coenzyme for enzymes involved in carboxylation reactions, has the structure

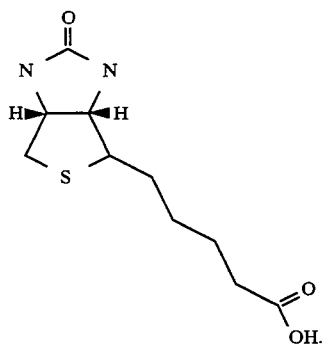

Intrinsically, it has very high affinity for streptavidin and avidin, the proteins derived from *Streptomyces avidinii* and egg white, respectively. The combination of either one of these proteins and biotin has been used as a marker system in immunoassays as well as in DNA probes. See Khosravi et al., "Novel Application of Streptavidin-Hapten Derivatives as Protein-Tracer Conjugate in Competitive-Type Immunoassays Involving Biotinylated Detection Probes", *Clin. Chem.*, 37/1, pp. 58–63 (1991) and Strasburger and Kohen, "Chemiluminescent Labelled Streptavidin (STAV) as a Universal Marker in Steroid and Peptide Immunoassays," *Journal of Bioluminescence and Chemiluminescence*, vol. 4, pp. 112–188. Avidin is a basic glycoprotein of ~68 kDa, has an exceptionally high binding affinity ($10^{15}$ L.mol$^{-1}$) for biotin.

The function of chemiluminescent labels in assay applications involves the coupling of the label compound to a substrate molecule. Such coupling can be achieved by solvent interfaction (e.g., molecular compatibility), any heterolytic or homolytic mechanism induced by chemical means and influenced by physical effects, such as time, temperature and/or mass action. For example, the reaction can be nucleophilic or electrophilic, or it can involve free radical mechanisms. In the broadest perspective, the coupling can be viewed as achievable via strong to weak bonding forces.

A chemiluminescent label in assays is an associated moiety of a binding material. The moiety is derived from a chemical compound which, as such, possesses chemiluminescent capabilities. Hereinafter, the term moiety as applied to the label as such, is a reference to the compound prior to being associated with a binding material. The term associated is intended to include all or any of the mechanisms for coupling the label to the substrate molecule.

The term "functional" in chemistry typically refers to a group that influences the performance of a chemical or constitutes the site for homolytic or heterolytic reactions. For example, a functional alkyl substituent, used in the context of interreactions through that substituent, means an alkyl group substituted so that it can effect that reaction. But an alkyl group termed functional for the electronic effects it induces in the molecule is a reference to the alkyl group per se.

THE INVENTION

This invention relates to a unique class of chemiluminescent labels containing biotin substitution that are suitable chemiluminescent assays using inter alia a streptavidin and/or avidin conjugate. The chemiluminescent labels of the invention have the ability to conjugate to streptavidin and/or avidin per se or to streptavidin and/or avidin conjugated with an analyte. Label structures are disclosed that have good hydrolyric stability to meet the most demanding commercial assay conditions. The invention encompasses conjugates containing associated versions of the labeling compounds, assays and kits for performing such assay utilizing the conjugates. The assays of the invention are useful for essentially any immunoassay, either of the competitive or non-competitive types.

The chemiluminescent biotinylated label compounds of the invention are any biotinyl substituted heterocyclic moiety having the capacity of exhibiting chemiluminescence when reacted with hydrogen peroxide in the presence of a base. The basic chemiluminescent label structure of the invention, prior to conjugation, has the formula:

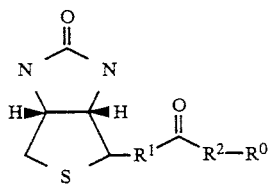

wherein $R^1$ is a divalent organic group, preferably aliphatic and containing from 1 to about 10 carbon atoms, most preferably containing at least 5 carbon atoms; and $R^2$ is an optional substituent of the biotin and when present it is a divalent moiety containing at least 1 carbon atom, preferably at least 5 carbon atoms, and in the typical case, will contain heteroatoms, such as nitrogen and oxygen. $R^2$ may be a repeating unit formed by nucleophilic substitution of biotin with a compound or compounds containing one or more complementary functional group that react with the structure containing the biotin moiety. $R^0$ comprises a heterocyclic structure and is directly bonded to the biotin or substituted biotin.

Particularly preferred embodiments of the label compounds of the invention include the following biotinylated heterocyclic compounds:

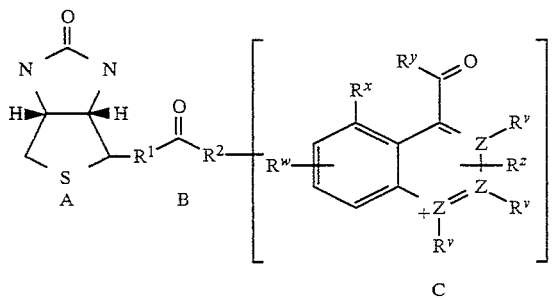

wherein A is the biotin moiety, B is an $R^1$ and the optional $R^2$, as defined above, and C is a heterocyclic fused ring possessing chemiluminescent properties, $R^v$, $R^w$ and $R^x$ may be hydrogen, carbon bonded amino, carbon bonded carboxy, carbon bonded halogen, carbon bonded sulfonyl, carbon bonded hydroxyl, carbon bonded amido, carbon bonded thiol, and monovalent organo bonded directly to carbon or nitrogen, as the case may be, $R^y$ is either an aryl substituted oxy, aryl substituted sulfide moiety, or an organosubstituted sulfonimino moiety bonded to the adjacent carbonyl by an oxygen, sulfur or nitrogen bond, as the case may be, one of the Z's is nitrogen, and the remainder are carbon, provided that one of $R^v$, $R^w$, $R^x$ and $R^y$ is directly bonded to $R^2$, if present, or to $R^1$ thereby linking A to C and the $R^v$ that is bonded to a Z that is nitrogen is bonded to that nitrogen by a carbon to nitrogen bond and, optionally, the $R^v$ that are bonded to carbon join to form an aromatic fused ring structure, such as acridinium and phenanthridinium.

More preferred are the biotinylated structures of the formula

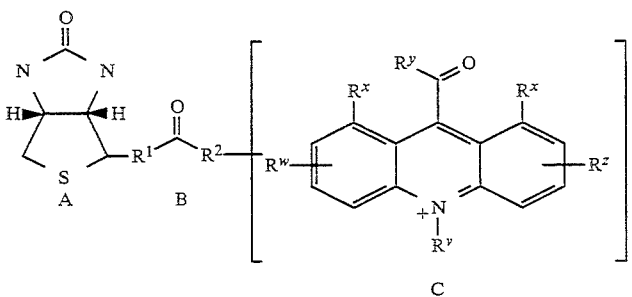

where the $R^{v-z}$ and $R^{1-2}$ have the definitions set forth above. Particularly desirable are the compounds encompassed by the formula:

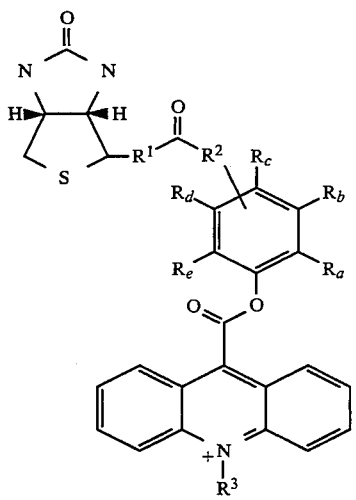

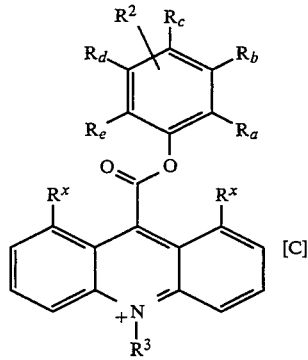

where $R^2$ is defined above, and when present, is bonded to one of $R_{a\text{-}e}$; and when $R^2$ is not present, the carbonyl is bonded to one of $R_{a\text{-}e}$; and $R_{a\text{-}e}$ are individually one of hydrogen, alkyl or 1 to about 12 carbon atoms, aryl or fused aryl whereby to form a bis-aryl, dicycloaryl or tricycloaryl, cycloalkyl of 5–8 carbon atoms, or a functional group, either bonded directly to carbon of the ring or bonded indirectly through an inorgano or organo group to the ring, which functional group is covalently or ionically bonded to the biotin of A, optionally through $R^2$ or through the carbonyl of the biotin moiety.

A particularly desirable class of the above compounds are those of the formula:

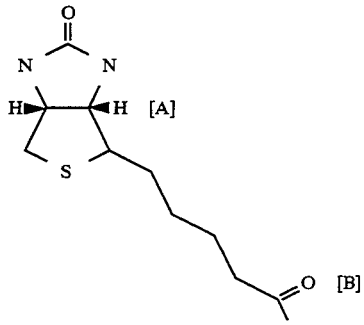

The invention encompasses a method for assaying the presence of an analyte in a sample. The method comprises contacting an analyte with the aforementioned chemiluminescent-labeled specific binding material (the "conjugate"), inducing chemiluminescence by decay of an intermediate dissodated from the conjugate, and measuring luminescence therefrom to assay the analyte.

In keeping with the inventive chemiluminescent-label's function of assaying, the invention embodies a specific binding assay kit comprising a vial containing a conjugate possessing chemiluminescent properties by chemically induced reaction and containing the aforementioned chemiluminescent label bonded to a specific binding material.

DETAILED DESCRIPTION OF THE INVENTION

Biotin's carboxylic acid moiety is a functional group that allows biotin to be coupled to other organic and inorganic compounds. For example, the carboxylic add may be reacted with N-hydroxysuccinimide (NHS) in the presence of a carbodiimide such as DCC. The resulting NHS ester can be reacted quite conveniently with a variety of complementary functional groups containing an active hydrogen suitable for entering into a nucleophilic reaction to form a nucleophilic reaction product. Illustrative of such groups are amines, hydroxyl (either alcoholic or aromatic hydroxyl), thiols, amide, urethane, carboxyl (to form stable anhydrides), and the like. Commercially available functionalized biotins include the following:

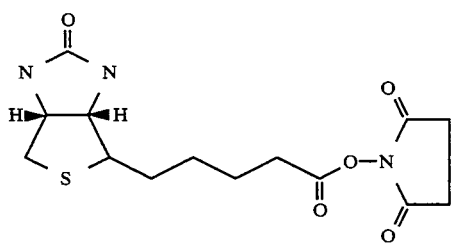

1.)

-continued

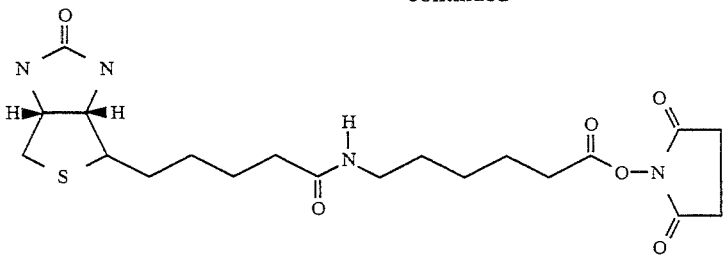

II.)

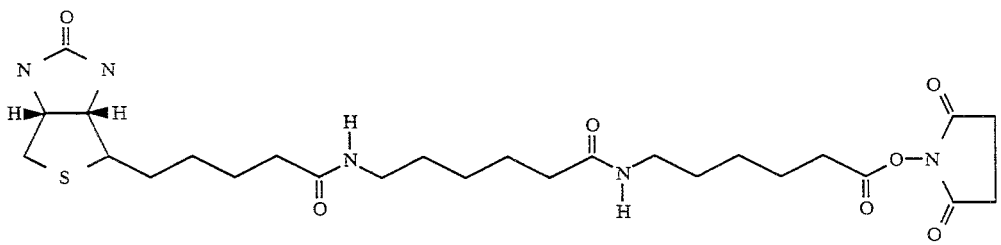

III.)

A particularly preferred class of biotinylated compound suitable for the practice of the invention, and creating a favorable intermediate in forming the chemiluminescent labels of the invention are the reaction products of NHS substituted biotin, such as described above, with amino acids, particularly those containing active hydrogen. For example, the reaction of I.) with lysine results in the structure called biocytin:

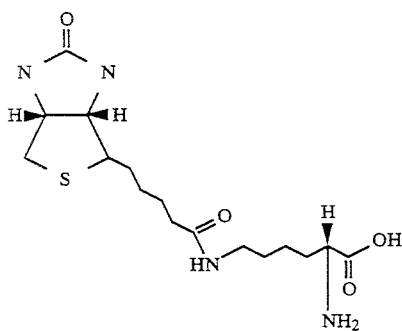

$N_E$-Biotinyl-L-Lysine

That reaction can be carried out with any of the amino acid, such as alanine, valine, leucine, isoleucine, tryptophan, phenylanaline, proline, methionine, glysine, serine, threonine, tyrosine, asparagine, glutamine, cysteine, lysine, arginine, histidine, aspartic acid and glutamic acid. The reaciton is carried out with any of the aminocarboxylic acids, hydroxycarboxylic acids, mercaptocarboxylic acids, and the like. Particularly preferred are the reaction products of the 20 natural amino acids making up proteins with the NHS esters of biotin. That reaction is illustrated below. It is a reaction that can be carried out in a variety of solvents and at temperatures ranging from about −20° C. to about 100° C., with the reactants being present in stoichiometric proportions for the formation of the desired reaction product.

The reaction of the substituted biotin, such as any of compounds I.)–III.), or their reaction product with amino acids or other functional groups are carried out in a suitable solvent, such as water, nitriles, ethers, ketones, esters, at moderate temperatures from about −20° C. to about 100° C. for a sufficient time to assure the desired degree of reaction. The reaction product is recovered by precipitation, distillation, crystallization, and the like procedures. If desired, the product may be kept in the reaction medium and further reacted with the heterocyclic compound that provides the chemiluminescent capabilities.

The reaction of the functionalized biotin with the heterocyclic compound can be accomplished by using a heterocyclic compound that contains a functional group that is complementary to the functional group of the functionalized biotin. Illustrative of such compounds are the functional heterocyclic compounds disclosed in copending U.S. Patent applications Ser. No. 291,843, filed Dec. 29, 1988, now abandoned, Ser. No. 549,564, filed Jul. 6, 1990, now abandoned, Ser. No. 827,727, filed Jan. 29, 1990, now abandoned, and Ser. Nos. 859,956, 860,410, 859,995. 859,676, 859,955, 859,994, and 860,001, each filed Mar. 30, 1992 now U.S. Pat. Nos. 5,284,951; 5,321,136; 5,284,952; 5,283,334; 5,290,936; 5,281,712 and 5,338,841 respectively. Also included are the sulfonamides of European Patent Applications, publication nos. 0 273 115 and 0 257 541, which includes the following acridinium and phenanthridinium structures that can be reacted with the functionalized biotin and biotin containing compounds to form labels within the scope of this invention:

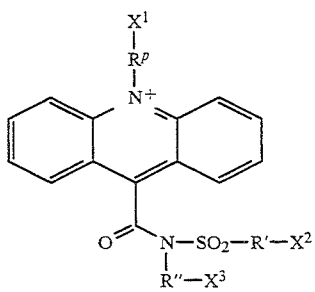

-continued

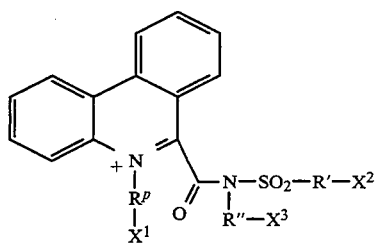

wherein $X^{1-3}$ may be a functional group that is reactable with the functional group of the biotin containing compound, or hydrogen, or a monovalent organic group, preferably containing less than about 12 carbon atoms. R', R" and $R^p$ are divalent organic groups, carbon bonded to the nitrogen and the sulfonyl. They may be aliphatic, aromatic, cycloalphatic, heterocyclic, and the like moieties.

Particularly desirable biotinylated chemiluminescent heterocyclic compounds are those encompassed by the formulae:

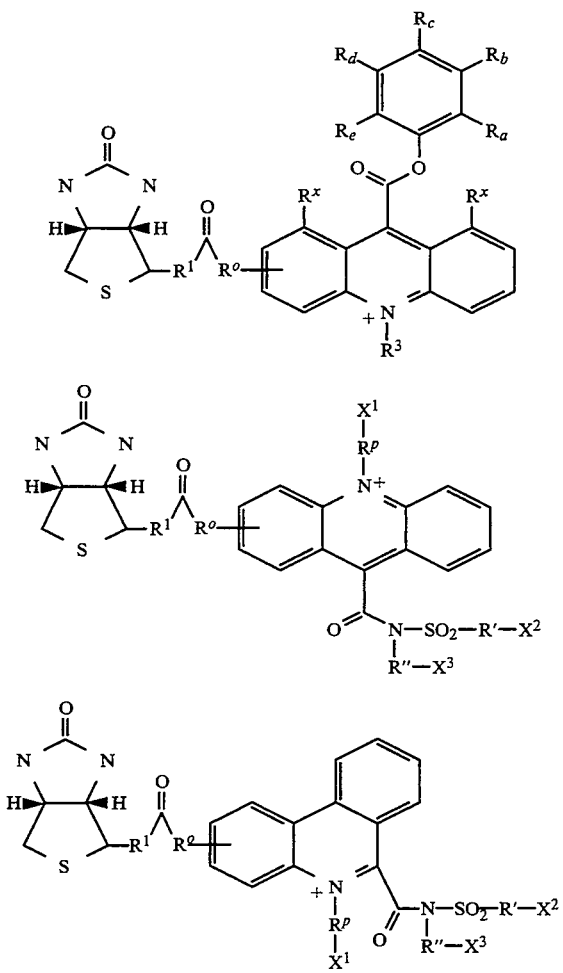

In these cases, the substituent groups are defined above. The reaction in this case involves a functional group $R^o$ bonded to the acridinium ring and the reaction of the functionalized biotin with it. In this case, $R^o$ comprises the functional group on the heterocyclic ring and the complementary group of the biotinyl compound coupled to it. For example, an amino substituted acridinium ester, where the amino is in either of the 2, 3 or 4 positions, may be reacted with one of the NHS substituted biotins illustrated above. However, if the functional group is an carboxy or sulfonyl type, then the biotin substitution will typically contain an amino or hydroxy substituent, such as provided by biocytin, biocytin hydrazide, and the like compositions.

The heterocyclic structure may contain suitable ring substitutions $R^w$ and $R^x$, may be functional or non-functional. Functionality can be for the purpose of enhancing the hydrolytic stability of the compound or for providing coupling capabilities via homolytic or heterolytic reactions or other forms of association that couple the label compound to its substrate. Such substitutions include those for the purposes of producing peri-interactions around the heterocyclic linkage to enhance the ester, thiolester or amide hydrolytic stability, providing functionality to the compound for coupling to proteins and other materials with complementary functionality, and increasing the compound's solubility and chemiluminescent efficiency. Groups useful for associating the compound to proteins and other materials so that the chemiluminescent label compounds of the invention function in a coupled state with them include, but are not limited to those described in the aforementioned copending patent applications.

Peri substituents include any group which can cause steric hindrance with respect to the carbon to which the ester, thiolester or amide linkage is attached and/or with respect to the carbon within the ester, thiolester of amide linkage. Preferred peri substituents include short alkyl groups ($C_{1-4}$, e.g., methyl, ethyl, and the like), aryl groups (e.g., phenyl), alkaryl (e.g., tolyl, xylyl, and the like), alkoxyalkyl ($C_{1-4}$ alkoxy, e.g., methoxymethyl, ethoxyethyl, and the like). The peri substituents, if present, are located on carbon atoms within the heterocyclic ring or ring system that are "adjacent to" the carbon to which the ester, thiolester or amide linkage is attached. Moieties can include more than one peri substituent. For example, peri substituents can be placed in the following positions:

1. in acridiniums and acridaris: on $C_1$ and $C_8$;
2. in phenanthridiniums and reduced phenanthridiniums: on $C_7$; and
3. in quinoliniums and reduced quinoliniums: on $C_3$.

The above-described improved chemiluminescent compounds are useful in a broad range of specific binding assays for the presence of analyte in a sample. "Presence" shall mean herein the qualitative and/or quantitative detection of an analyte. Such assays may be directed at any analyte which may be detected by use of the improved chemiluminescent compound in conjunction with specific binding reactions to form a moiety thereon. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes a chemiluminescent conjugate which comprises the improved chemiluminescent moiety attached to a specific binding material. "Specific binding material" means herein any material which will bind specifically by an immunoreaction, protein binding reaction, nucleic acid hybridization reaction, and any other reaction in which the material reacts specifically with a restricted class of biological, biochemical or chemical species. In this category of assays, the chemiluminescent conjugate participates in a specific binding reaction and the presence of analyte in the sample is proportional to the formation of one or more specific binding reaction products containing the chemiluminescent conjugate. The assay is performed by allowing the requisite specific binding reactions to occur under suitable reaction conditions. The formation of specific binding reaction products containing the chemiluminescent conjugate is determined by measuring the chemiluminescence of such products containing the chemiluminescent conjugate or by measuring the chemiluminescence of unreacted or partially reacted chemiluminescent conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent moiety is attached, is capable of specifically binding with the analyte. The assay further utilizes a reactant which is capable of specifically binding with the analyte to form a reactant-analyte-chemiluminescent conjugate complex. The reactant may be attached to a solid phase, including without limitation, dip sticks, beads, tubes, paper or polymer sheets. In such cases, the presence of analyte in a sample will be proportional to the chemiluminescence of the solid phase after the specific binding reactions are completed. Such assay formats are discussed further in U.S. Pat. Nos. 4,652,533, 4,383,031, 4,380,580 and 4,226,993, which are incorporated herein by reference.

In a competitive format, the assay utilizes a reactant which is capable of specifically binding with the analyte to form an analyte-reactant complex and with the specific binding material, to which the chemiluminescent moiety is attached, to form a chemiluminescent conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the chemiluminescence of the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-chemiluminescent conjugate complex formed as a reaction product. This is illustrated by attaching the chemiluminescent moiety via a streptavidin moiety to antibody which is specific to a surface antigen on a cell. The presence of the cell surface antigen will be indicated by the chemiluminescence of the cells after the completion of the reaction. The cells themselves may be used in conjunction with a filtration system to separate the analyte-chemiluminescent conjugate complex which is formed on the surface of the cell from unreacted chemiluminescent conjugate. This is discussed further in U.S. Pat. No. 4,652,533.

The improved chemiluminescent moiety may be used in additional assay formats known in the art including without limitation sequential saturation and competitive displacement, both of which utilize a chemiluminescent conjugate where both (1) the specific binding material, to which the moiety is attached, and (2) the analyte specifically bind with a reactant. In the case of sequential saturation, the analyte is reacted with the reactant first, followed by a reaction of the chemiluminescent conjugate with remaining unreacted reactant. In the case of competitive displacement, the chemiluminescent conjugate competitively displaces analyte which has already bound to the reactant.

In a quenching format, the assay utilizes a reactant which is capable of specifically binding with the analyte to form an analyte-reactant complex and with the specific binding material, to which the chemiluminescent moiety is attached, to form a chemiluminescent conjugate-reactant complex. A quenching moiety is attached to the reactant. When brought into close proximity to the chemiluminescent moiety, the quenching moiety reduces or quenches the chemiluminescence of the chemiluminescent moiety. In this quenching format, the presence of analyte is proportional to the chemiluminescence of the chemiluminescent moiety. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the chemiluminescent conjugate may be reacted with the complex on the solid phase. Alternatively, the solid phase, sample and chemiluminescent conjugate may be added together simultaneously and reacted prior to separation. As a still further but less preferred alternative, the analyte in the sample and the chemiluminescent conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated improved chemiluminescent compound. The presence of analyte in the sample is proportional to the formation of one or more specific binding reaction products which do not themselves contain the chemiluminescent moiety. Instead, the chemiluminescent compound chemiluminesces in proportion to the formation of such reaction products. In one example of this second category of assays, the assay utilizes a reactant capable of binding with the analyte to form an analyte-reactant complex which causes the chemiluminescent compound to chemiluminesce.

The assays contained in the above categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-chemiluminescent conjugate complex is separated from unreacted chemiluminescent conjugate. In a surface antigen assay, the analyte-chemiluminescent conjugate complex is separated from unreacted chemiluminescent conjugate. In a competitive assay, the reactant-chemiluminescent conjugate complex is separated from unreacted chemiluminescent conjugate. In a sequential saturation assay and in a competitive displacement assay, the reactant-chemiluminescent conjugate complex is separated from unreacted chemiluminescent conjugate. Alternatively, in homogeneous assays the reaction products are not separated. After the assay reagents have been allowed to react, the chemiluminescence may be measured from the whole assay mixture whether such mixture is in solution, on a solid phase or distributed between various membrane layers of a dip stick or other solid support.

Finally, "measuring the chemiluminescence" shall include, where relevant, the act of separating those specific binding reaction products, the formation of which are proportional to the presence of analyte in the sample, from other reaction products. It shall also include, where relevant, the acts of triggering the chemiluminescent moiety to chemiluminesce in the case of those assay formats in which the formation of the reaction products does not itself trigger the chemiluminescent moiety.

Synthesis Of Labels

The following examples show the synthesis of certain chemiluminescent labels of the present invention. These chemiluminescent labels are typically made in small quantities and the procedures employed for their manufacture do not reflect conventional large scale chemical manufacturing procedures. In these reactions, conventional reactions have been employed to produce the chemiluminescent labels of the invention. Purification procedures suitable for isolating product are conventional laboratory procedures, such as crystallization out of solvent solution by the addition of a nonsolvent, solvent extraction, and the like. In such cases, many different solvents and nonsolvents are suitable. Yields are the amounts recovered as a percentage of reactants employed.

EXAMPLE 1

Biocytin (0.3 mg, 0.08 m mole) was dissolved in bicarbonate buffer (15 mM, pH 9.6, 100 μL). 2,6-Dimethyl-3-chlorosulfonyl phenyl acridinium-9-carboxylate fluorosulfonate (0.28 mg, 0.05 mmole) was dissolved in DMF (100 μL and bicarbonate buffer (25 μL) was added. The two solutions were mixed together and allowed to stand at room temperature. The reaction mixture was monitored in a C-18 reverse phase column using a HPLC System. The products were detected at 363 nm. An elution solvent of a 9:1 mixture by volume of acetonitrile and water containing 0.1% trifluoroacetic acid was used. The peak corresponding to a product distinct from the starting acridinium ester or its hydrolyzed form was collected and solvents were evaporated.

The biotinyl-acridinium [2,6-dimethyl-3 (N$_E$-Biotinyl-L-Lysyl sulfonyl) phenyl N-methyl-acridinium-9-carboxylate] BA was tested in an

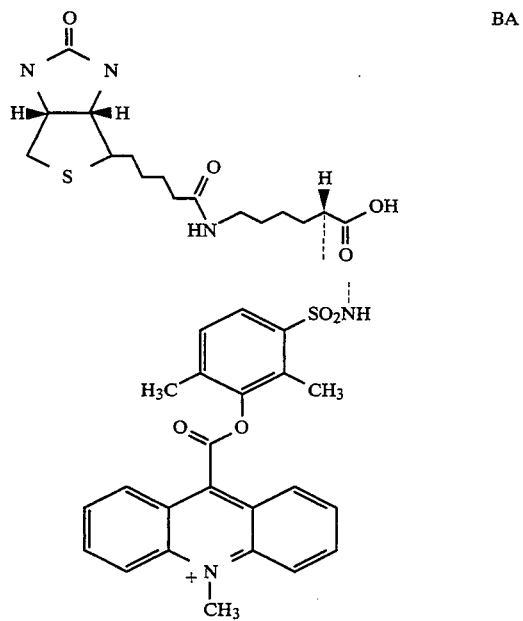

immunoassay system for quantifying progesterone using a streptavidin progesterone conjugate.

A goat anti-rabbit antibody coated bead was incubated for 4 hours at room temperature with rabbit anti progesterone antibody (50 μL, a 1:60,000 dilution from stock), progesterone containing standards (50 μL, in steroid-free human serum; 0, 0.1, 0.5, 2.0, 10.0, 20.0 and 40.0 ng/mL), streptavidin-progesterone conjugate (50 μL and biotynyl acridinium [BA] (100 μL, phosphate buffer, pH 6.0). At the end of four hours, the bead was washed and counted in a Berthold ® luminometer. The following data was obtained.

| ng/mL | RLU | Mean | % CV | B/B$_o$ |
|---|---|---|---|---|
| 0 | 25789 | 26126 | 10 | 100% |
| | 26464 | | | |
| 0.1 | 22829 | 22781 | 0.2 | 87% |
| | 22734 | | | |
| 0.5 | 17015 | 16902 | 0.6 | 64% |
| | 16789 | | | |
| 2.0 | 9878 | 9817 | 0.6 | 37% |
| | 9757 | | | |
| 10.0 | 3923 | 4004 | 2.0 | 15% |
| | 4085 | | | |

-continued

| ng/mL | RLU | Mean | % CV | $B/B_o$ |
|---|---|---|---|---|
| 20.0 | 2674 | 2745 | 2.5 | 10% |
|  | 2816 |  |  |  |
| 40.0 | 1830 | 1816 | 0.7 | 7% |
|  | 1803 |  |  |  |

EXAMPLE 2

Biocytin (6 mg, 1.6 m mole) was dissolved in acetonitrile (400 μL) and dibasic sodium phosphate (0.1 M, 1 mL) was added. 2,6-Dimethyl-3-chlorosulfonyl phenyl acridinium-9-carboxylate (5.2 mg., 0.93 mmole) was dissolved in acetonitrile (400 μL) and dibasic sodium phosphate solution (0.01 M, 400 μL) was added. The two solutions were mixed together and allowed to stand at room temperature for 2 hours. The reaction product was isolated in a C-18 reverse phase column using a HPLC System. An elution solvent of a 9:1 mixture by volume of acetonitrile and water containing 0. 1% trifluoroacetic acid was used. The peak corresponding to a product distinct from the starting acridinium ester or its hydrolyzed form was collected and solvents were evaporated.

I claim:

1. A chemiluminescent label compound containing a biotin substituent that forms a streptavidin or avidin complex, having the formula:

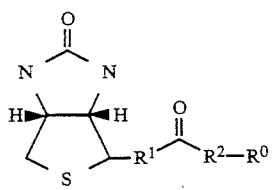

in which $R^1$ is a divalent organic group; and $R^2$ is an optional substituent of the biotin and when present it is a divalent moiety containing at least 1 carbon atom; and $R^0$ is a heterocyclic structure directly bonded to the biotin or substituted biotin, that has the capacity of exhibiting chemiluminescence when reacted with hydrogen peroxide in the presence of a base.

2. The chemiluminescent label compound of claim 1 complexed to streptavidin, avidin or to streptavidin or avidin complexed with an analyte.

3. The chemiluminescent label compound of claim 1 possessing hydrolytic stability.

4. In an diagnostic assay for the detection of an analyte using a chemiluminescent label conjugated to a specific binding material, the improvement wherein the label is the chemiluminescent label compound of claim 1.

5. A chemiluminescent labeled conjugate comprising the chemiluminescent label compound of claim 1 conjugated with a specific binding material.

6. The diagnostic assay of claim 4 wherein said assay is a competitive or non-competitive immunoassay.

7. The chemiluminescent label compound of claim 1 wherein $R^1$ is an aliphatic group that contains from 1 to about 10 carbon atoms.

8. The chemiluminescent label compound of claim 7 wherein $R^1$ is an aliphatic group that contains at least 5 carbon atoms.

9. The chemiluminescent label compound of claim 1 wherein $R^2$ contains at least 5 carbon atoms.

10. The chemiluminescent label compound of claim 10 wherein $R^2$ comprises heteroatoms.

11. The chemiluminescent label compound of claim 10 wherein heteroatoms include nitrogen or oxygen.

12. The chemiluminescent label compound of claim 1 wherein $R^2$ is a repeating unit formed by nucleophilic substitution of biotin with a compound or compounds containing one or more complementary functional group that react with the structure containing the biotin moiety.

13. A chemiluminescent label compound having the biotinylated heterocyclic structure:

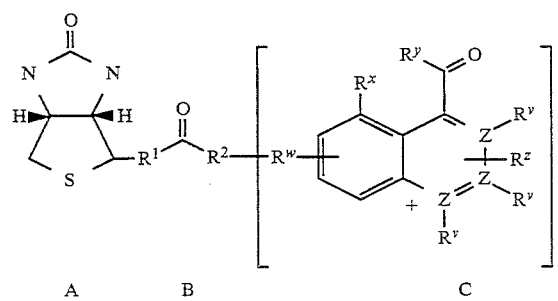

wherein A is a biotin moiety, B is $R^1$ and an optional $R^2$, $R^1$ is a divalent organic group; and $R^2$ is an optional substituent of the biotin and when present it is a divalent moiety containing at least 1 carbon atom; and C is a heterocyclic fused ring that has the capacity of exhibiting chemiluminescence when reacted with hydrogen peroxide in the presence of a base, each $R^v$, $R^w$ and $R^x$ is hydrogen, carbon bonded amino, carbon bonded carboxy, carbon bonded halogen, carbon bonded sulfonyl, carbon bonded hydroxyl, carbon bonded amido, carbon bonded thiol, or monovalent organo bonded directly to carbon or nitrogen, as the case may be, $R^y$ is either an aryl substituted oxy, aryl substituted sulfide moiety, or an organosubstituted sulfonimino moiety bonded to the adjacent carbonyl by an oxygen, sulfur or nitrogen bond, as the case may be, one of the Z's is nitrogen, and the remainder are carbon, provided that one of $R^v$, $R^w$, $R^x$ and $R^y$ is directly bonded to $R^2$, if present, or to $R^1$, thereby linking A to C and the $R^v$ that is bonded to a Z that is nitrogen is bonded to that nitrogen by a carbon to nitrogen bond and, optionally, the $R^V$ that are bonded to carbon join to form an aromatic fused ring structure.

14. The chemiluminescent label compound of claim 13 wherein the heterocyclic fused ring is acridinium and phenanthridinium.

15. The chemiluminescent label compound of claim 14 wherein the heterocyclic fused ring is acridinium.

16. The chemiluminescent label compound of claim 14 wherein the heterocyclic fused ring is phenanthridinium.

17. The chemiluminescent label compound of claim 15 wherein the biotinylated heterocyclic structure has the formula:

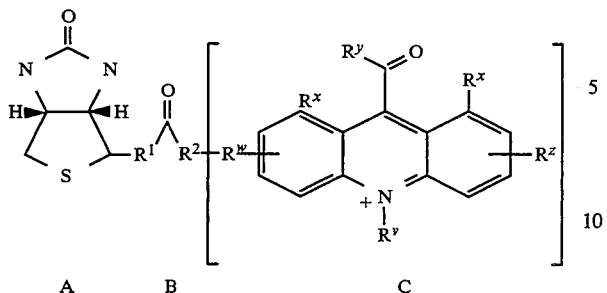

A   B   C

18. The chemiluminescent label compound of claim 17 wherein the biotinylated heterocyclic structure has the formula:

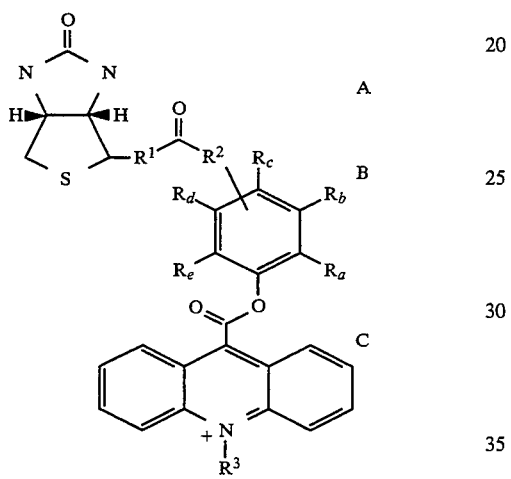

in which $R^2$, and when present, is bonded to one $R_{a-e}$; and when $R^2$ is not present, the carbonyl is bonded to one of $R_{a-e}$; and $R_{a-e}$ are individually one of hydrogen, alkyl or 1 to about 12 carbon atoms, aryl or fused aryl whereby to form a bis-aryl, dicycloaryl or tricycloaryl, cycloalkyl of 5–8 carbon atoms, or a functional group, either bonded directly to carbon of the ring or bonded indirectly through an inorgano or organo group to the ring, which functional group is covalently or ionically bonded to the biotin of A, optionally through $R^2$ or through the carbonyl of the biotin moiety.

19. In the diagnostic assay of claim 4 for the detection of an analyte using a chemiluminescent label conjugated to a specific binding material, in which the improvement uses the chemiluminescent label compound of claim 1 wherein the analyte is mixed with said chemiluminescent-labeled specific binding material, chemiluminescence is induced by decay of an intermediate dissociated from the conjugate, and luminescence therefrom is measured to assay the analyte.

20. In a kit for diagnostic assaying in which is provided a vial containing a labeled complex possessing chemiluminescent properties that diagnoses an analyte by measuring the chemiluminescence caused by the decay of the label, the improvement wherein the complex is the complex of claim 2.

21. The chemiluminescent label compound of claim 17 wherein the biotinylated heterocyclic structure has the formula:

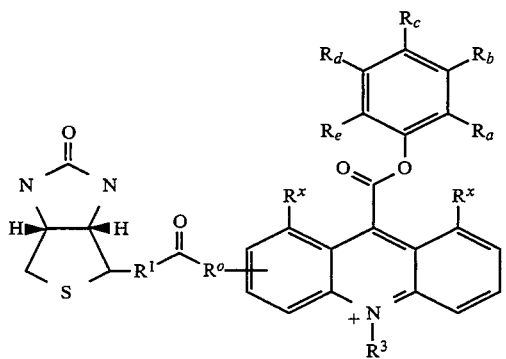

22. The chemiluminescent label compound of claim 18 wherein the biotinylated heterocyclic structure has the formula:

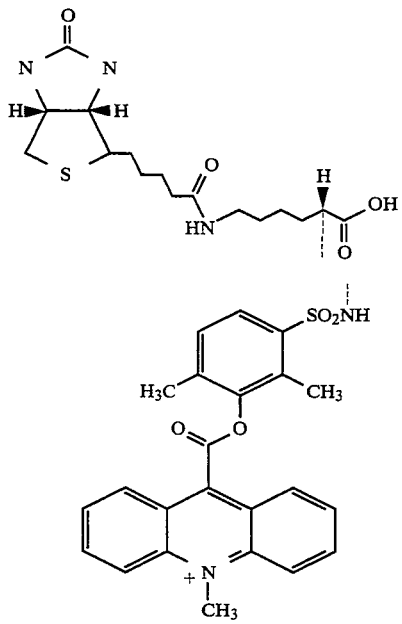

23. The process of making a biotinylated chemiluminescent label of claim 1 which comprises reacting a functional biotin containing compound and chemiluminescent heterocyclic compound that has the capacity of exhibiting chemiluminescence when reacted with hydrogen peroxide in the presence of a base.

24. The process of claim 23 wherein the biotin is a NHS substituted compound.

25. The process of claim 24 wherein the biotin is one of the compounds of the formulae:

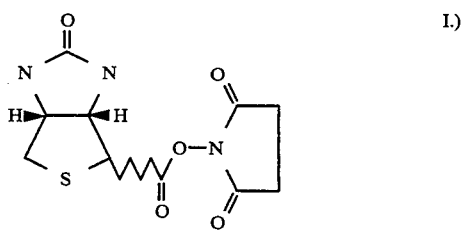

I.)

-continued

II.)

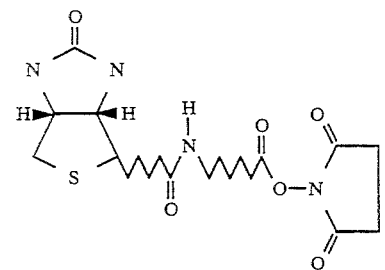

III.)

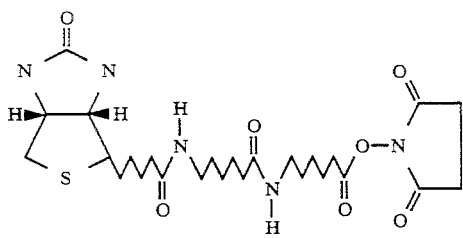

26. The process of claim 23 wherein the biotin is coupled to an amino acid.

27. The process of claim 26 wherein the amino acid is lysine.

28. The process of claim 27 wherein the biotin reacted with lysine has the formula:

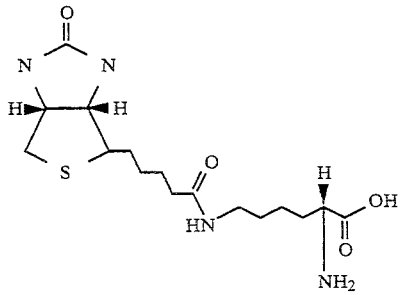

29. The process of claim 23 wherein the chemiluminescent heterocyclic compound is a sulfonamide having one of the formulae:
wherein each $X^{1-3}$ is one of a functional group that is reactable with the functional group of the biotin containing compound, or hydrogen, or a monovalent organic group, and R′, R″ and $R^p$ are divalent organic groups, carbon bonded to the nitrogen and the sulfonyl.

* * * * *

UNITED STATES PATENT AND TRADEMARK OFFICE
CERTIFICATE OF CORRECTION

PATENT NO. : 5,395,938
DATED : March 7, 1995
INVENTOR(S) : Kastooriranganathan Ramakrishnan It is certified that error appears in the above-indentified patent and that said Letters Patent is hereby corrected as shown below:

At column 18, line 2, changed "10" to read ----9----;

Signed and Sealed this

Twentieth Day of February, 1996

Attest:

BRUCE LEHMAN

Attesting Officer

Commissioner of Patents and Trademarks